US010359280B2

(12) United States Patent
Bai et al.

(10) Patent No.: US 10,359,280 B2
(45) Date of Patent: Jul. 23, 2019

(54) 3-D AIR POLLUTION TRANSMISSION PATH IDENTIFICATION

(71) Applicant: International Business Machines Corporation, Armonk, NY (US)

(72) Inventors: Xin Xin Bai, Beijing (CN); Xin Jie Lv, Beijing (CN); Xiao Guang Rui, Beijing (CN); Xi Xia, Beijing (CN); Jian Yao, Beijing (CN); Wen Jun Yin, Beijing (CN); Wei Zhao, Beijing (CN); Yu Xin Zhao, Shanghai (CN)

(73) Assignee: International Business Machines Corporation, Armonk, NY (US)

( * ) Notice: Subject to any disclaimer, the term of this patent is extended or adjusted under 35 U.S.C. 154(b) by 104 days.

(21) Appl. No.: 15/581,981

(22) Filed: Apr. 28, 2017

(65) Prior Publication Data
US 2018/0313648 A1 Nov. 1, 2018

(51) Int. Cl.
*G01B 21/20* (2006.01)
*G01B 21/16* (2006.01)
*G01N 33/00* (2006.01)

(52) U.S. Cl.
CPC ............. *G01B 21/20* (2013.01); *G01B 21/16* (2013.01); *G01N 33/00* (2013.01)

(58) Field of Classification Search
None
See application file for complete search history.

(56) References Cited

U.S. PATENT DOCUMENTS

| 5,831,876 A * | 11/1998 | Orr ......................... G06T 17/05 |
| | | 703/6 |
| 9,317,732 B2 | 4/2016 | Gong et al. |
| 2013/0179100 A1* | 7/2013 | Guo ................... G01R 31/1227 |
| | | 702/59 |
| 2016/0314256 A1* | 10/2016 | Su .......................... G06F 19/345 |

(Continued)

FOREIGN PATENT DOCUMENTS

| JP | 2013531244 A | 8/2013 |
| WO | WO 2011/002272 A1 | 1/2011 |

OTHER PUBLICATIONS

M. L. Akinyemi ( Dynamics of Wind Strength and Wind Direction on Air Pollution Dispersion, vol. 04—Issue 02, Apr. 2016, pp. 422-429).*

(Continued)

*Primary Examiner* — Tung S Lau
(74) *Attorney, Agent, or Firm* — Scully, Scott, Murphy & Presser, P.C.; Grant Johnson, Esq.

(57) ABSTRACT

A system, method and computer program product for tracking and identifying a polluted air mass's transmission trajectory in real 3-D space. In one aspect, a polluted air mass's transmission path identification is based on a monitoring of PM2.5 concentration in cubic volumes of an air mass. The method computes a transmission path of polluted air that considers wind-pressure conversion, the displacement estimation with mass concentration, and planetary boundary layer (PBLP height constraint) for 3-D cubic grids. The resultant determination of a polluted air mass's transmission trajectory in real 3-D space generates more practical and reliable results for intensive knowledge of the transport pathways and potential pollution sources in real 3-D space.

14 Claims, 8 Drawing Sheets

(56) References Cited

U.S. PATENT DOCUMENTS

2017/0108236 A1* 4/2017 Guan .................. G05B 19/04

OTHER PUBLICATIONS

Ujang, Uznir (Unified Data Model of Urban Air Pollution Dispersion and 3D Spatial City Models: Groundwork Assessment towards Sustainable Urban Development for Malaysia, 2013, p. 1-11).*
G. Wang (Modelling Urban Traffic Air Pollution Dispersion, 2008, p. 153-158).*
Khaled Ahmad Ali Abdulla Al Koas ( GIS-based Mapping and Statistical Analysis of Air Pollution and Mortality in Brisbane, Australia , Apr. 2010, pp. i-67).*
Nan Sheng (Prediction and 3D Visualization of Environmental Indicators: Noise and Air Pollution, Dec. 2011, 88 pages).*
Huan Li (A Visualization Approach to Air Pollution Data Exploration—A Case Study of Air Quality Index (PM2.5) in Beijing, China, Atmosphere 2016, 7, 35; doi:10.3390/atmos7030035, 20 pages ).*
List of IBM Patents or Patent Applications Treated as Related.
English language translation of JP 2013531244.
Hu et al., "Estimating ground-level PM2.5 concentrations in the Southeastern United States using MAIAC AOD retrievals and a two-stage model", Remote Sensing of Environment, 140, received Feb. 26, 2013, available online Sep. 26, 2013, pp. 220-232.
Van Donkelaar et al., "Estimates of Ambient Fine Particulate Matter Concentrations from Satellite-Based Aerosol Optical Depth: Development and Application", Environmental Health Perspectives, vol. 118, No. 6, Jun. 2010, pp. 847-855.

* cited by examiner

AIR DENSITY TABLE

| PRESSURE | TEMPERATURE | AIR DENSITY | PRESSURE | TEMPERATURE | AIR DENSITY |
|---|---|---|---|---|---|
| Mpa | DEGREE CELSIUS (°C) | Kg/m3 | Mpa | DEGREE CELSIUS (°C) | Kg/m3 |
| 0.1 | 25 | 1.1691 | 1.4 | 25 | 16.367 |
| 0.2 | 25 | 2.3381 | 1.5 | 25 | 17.537 |
| 0.3 | 25 | 3.5073 | 1.6 | 25 | 18.706 |
| 0.4 | 25 | 4.6764 | 1.7 | 25 | 19.875 |
| 0.5 | 25 | 5.8455 | 1.8 | 25 | 21.044 |
| 0.6 | 25 | 7.0146 | 1.9 | 25 | 22.213 |
| 0.7 | 25 | 8.1837 | 2.0 | 25 | 23.382 |
| 0.8 | 25 | 9.3528 | 2.1 | 25 | 24.551 |
| 0.9 | 25 | 10.522 | 2.2 | 25 | 25.720 |
| 1.0 | 25 | 11.691 | 2.3 | 25 | 26.889 |
| 1.1 | 25 | 12.860 | 2.4 | 25 | 28.058 |
| 1.2 | 25 | 14.029 | 2.5 | 25 | 29.228 |
| 1.3 | 25 | 15.198 | | | |

# 3-D AIR POLLUTION TRANSMISSION PATH IDENTIFICATION

FIELD

The present application relates generally to systems and methods for monitoring air pollution, and more particularly, to methods, apparatuses, and systems for performing 3D-air pollution transmission path identification with 3-D pollution monitoring data.

BACKGROUND

Air pollution, e.g., in the form of a heavy haze, often appear in large areas of a city or country. Current work in monitoring such pollution is based on 2-D observed pollution data from ground monitoring sites.

A certain type of air pollution includes presence of particulate matter (PM) of various sizes. Fine particular matter, e.g., particles less than 2.5 μm (micrometers) in diameter is referred to as PM2.5.

Based on 2-D observed pollution data from ground monitoring sites, the transport pathways of PM25 can be identified by methods such as pollution correlation analysis.

Currently, a 2D-air pollution transmission path may be identified based on observed pollution data in monitored sites. For example, 2D-air pollution transmission path can be identified by a backward trajectory method.

Other current techniques for investigating the transport pathways and potential sources of PM25 based on monitoring data uses three methods: backward trajectory cluster analysis, trajectory sector analysis (TSA) and potential source contribution function (PSCF).

SUMMARY

A system, method and computer program product for identifying a 3-D air pollution transmission path based on 3-D pollution monitoring data.

In one aspect, there a computer-implemented method for determining a main transmission path of a polluted air mass comprises: determining, by a processor, a current 3-D contour of pollution at an initial location and an initial time instant, the current 3-D contour having one or more cubic volumes of polluted air based on measured particulate concentration levels of an air mass at the initial location; computing, by the processor, based on received wind field condition data, an estimated 3-D contour of pollution for a next time instant and at a next destination location, the next destination determined based on estimated transport destinations of one or more cubic volumes of polluted air of the current 3-D contour from the initial location due to a wind field condition; determining, by the processor, a next current 3-D contour of pollution at the next destination location and at the next time instant, the next current 3-D contour having one or more cubic volumes of polluted air based on new measured particulate concentration levels of an air mass at the next destination location; and determining, by the processor, a transport path of the polluted air mass from the initial location to the next destination location at the next time instant, the determining based on a degree of transport weight overlap between cubic volumes of polluted air corresponding to the estimated 3-D contour of pollution at the next destination location and cubic volumes of polluted air corresponding to the determined current 3-D contour at the next time instant.

Other embodiments include a computer program product and a system.

BRIEF DESCRIPTION OF THE SEVERAL VIEWS OF THE DRAWINGS

The foregoing aspects and other features are explained in the following description, taken in connection with the accompanying drawings, wherein:

FIG. 9 shows an example air density table showing example air temperature and pressure conditions and corresponding air density computations.

DETAILED DESCRIPTION

A system and method provides for the identification and detection of patterns for air pollution moving under 3-D meteorological conditions. Using the system/methods herein, one can find a main potential pollution source and transport pathways so that the potential source, like industrial factory or traffic ways, can be optimally controlled.

Figure 1:
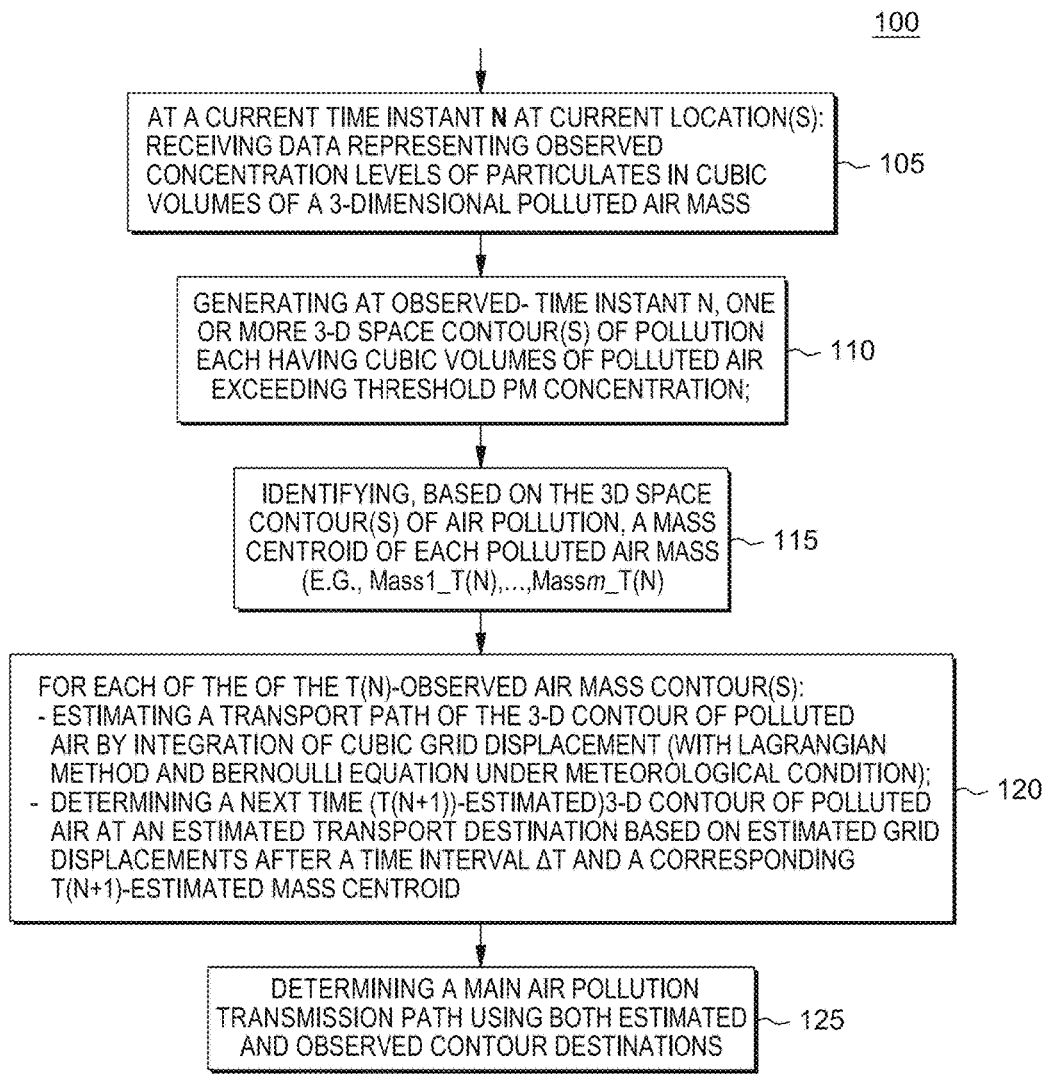
FIG. 1 is a flowchart illustrating a first exemplary method for identifying a 3D air pollution path in accordance with one or more embodiments of the present invention.

FIG. 1 is a flowchart illustrating a first exemplary method 100 for identifying a 3D-air pollution transmission path using 3-D pollution monitoring data.

In one embodiment, a first method step 105 includes obtaining, at a first or current time instant, data representing observed locations of particulate matter (PM) in a 3-dimensional (3-D) grid of cubic volumes of an air mass. In one embodiment, particulate matter may include PM2.5. Monitoring of these particle concentration levels in the 3-D volume may be obtained using, for example, UAV (Unmanned Aerial Vehicle) having sensors that can monitor a volume of air in three dimensions to obtain a PM2.5 concentration data. Further, vehicle-mounted laser radar may be implemented to detect in a vertical dimension, a PM2.5 distribution in different layers of heights. Using the obtained 3-D PM2.5-pollution monitoring data, a 3-D cubic grid data of PM2.5 observed concentration is obtained, e.g., by interpolation.

With the received 3-D monitoring data, intensive knowledge of the transport pathways and potential sources in real 3-D space of PM2.5 is used to effectively control PM2.5 pollution. After obtaining data from sensors representing observed locations of particulate matter in the 3-D volume of the atmosphere, the system determines, using a programmed processor, a concentration value of particles in the 3-dimension volume of the atmosphere. Then, based on the determined concentrations values of particles at locations in the 3-D space, the system identifies, at 110, a 3-D "space" contour of air pollution within a 3-dimension volume of the air mass. In one embodiment, as depicted, several 3-D air mass contours having cubic volumes of polluted air may be identified at a first time instant (e.g., observed-T1 time) (i.e., a time instant T(N)).

In one aspect, as will be described, each 3-D pollution air mass contour(s) can be recognized (observed particulate concentration) at period time intervals, e.g., on the hour, during a heavy pollution process based on 3-D pollution monitoring data.

Continuing to 115, the system further performs identifying based on the 3-D space contour of air pollution, a location of a centroid of the air mass. That is, method steps are employed at this step for selecting and calculating key features to evaluate the polluted air mass, like center relative location, length/width/height ratio, concentration distribution and its variation rate with distance.

Continuing to 120, for each of the current observed air mass contour(s), the system further performs estimating a transport of the air pollution mass by integration of cubic grid displacement with Lagrangian method and Bernoulli equation (wind-pressure relationship) in a 3-D meteorological condition. In one embodiment, the present methods provide for air transport transmission identification of a 3-D pollution contour in consideration of: 1) wind-pressure conversion, 2) displacement estimation with mass concentration, and 3) PBL height constraint for a 3-D grid. By accounting for these considerations, the system generates more practical and reliable results for intensive knowledge of the transport pathways and potential sources in real 3-D space.

For each of the observed-T(N) time 3-D pollution contour(s), and based on the integration of cubic grid displacements for a time interval Δt, the system then determines a corresponding time T(N+1)-estimated 3-D contour (estimated air mass destination grids) of polluted air at an estimated transport destination after a transport time Δt.

Finally at 125, the system further implements methods for determining a final destination and contour of the air pollution after transport. In one embodiment, as described herein with respect to FIG. 6, the final destination and contour of the polluted air mass may be determined with a transport weight by overlap degree between estimated air mass's destination grids and observed air mass grids. That is, for example, if several T1-observed masses transport and then merge into one T2-observed air mass, the transport weight of each path may be introduced from gird-overlap ratio to select the main path.

In one embodiment, the main 3-D air pollution transmission path can be identified by connecting the 3-D air mass's centroids at each transported location during successive time-instances. The 3-D air pollution transmission path identification with 3-D pollution data is more accurate by consideration of wind-pressure conversion, the displacement estimation with mass concentration, and PBL height constraint for 3-D grid.

Figure 2:
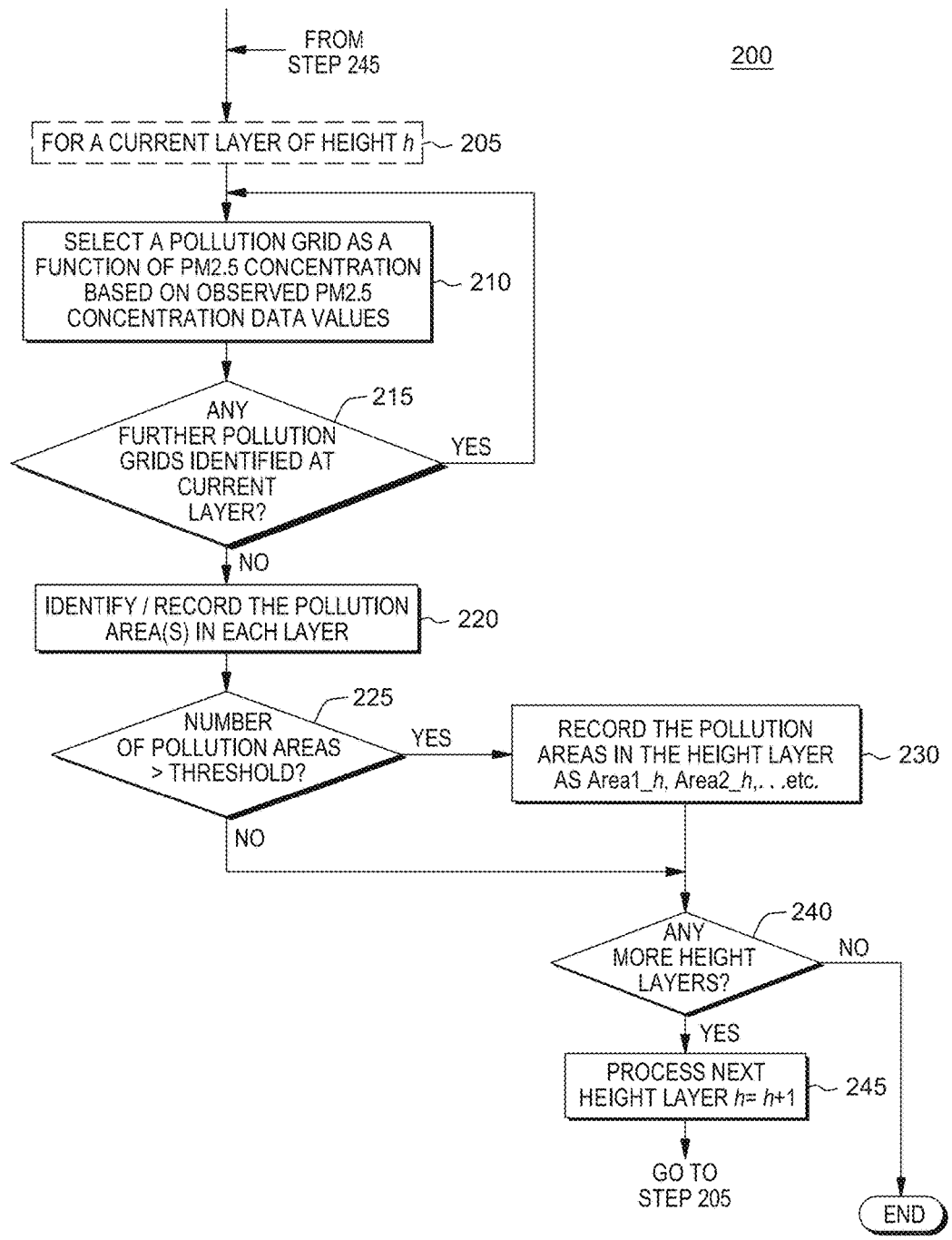
FIG. 2 conceptually illustrates an example 3-D contour identification and centroid extraction process 200.

FIG. 2 conceptually illustrates an example of a 3-D contour identification and centroid extraction process 200.

At a first step 205, a layer of height within a 3D cubic volume air mass, as constrained within a Plantary Boundary Layer (PBL) height (e.g., 300 m~1000 m), is selected. Then, at 210, the system methods perform a pollution grid extraction wherein, at a selected location (e.g., latitude and longitude coordinate) and a selected height ("h"), 3-D pollution grid(s) is(are) selected. In one embodiment, the determining of a pollution grid to select is by the observing of a concentration of the particulate matter at that height, e.g., as obtained from the UAV sensors, and determining that a concentration of particulate matter, e.g., PM2.5 in micrograms per cubic meter (e.g., $\mu g/m^3$), at that particular height is greater than a threshold concentration, i.e., $$PM2.5(lat,lon,height) > Thresh$$

Where lat and long is a coordinate of a specific location, height is the selected height h, and Thresh is a threshold particulate concentration value above which will assign a grid area at this height. This PM2.5 concentration value (as a function of lat, lon, value) is based on a 3-D cubic grid data of PM2.5 observed concentration.

At 215, a step is determined whether, for that current layer, there are any further pollution grids identified. If there are further identified pollution grids that can be identified in the current height layer, then the process returns back to 210 to select a next pollution grid at that current layer. If, at 215, it is determined that there are no further identified pollution grids that can be identified in the current height layer, then the process proceeds to 220, where a determination is made to identify and record the pollution "areas" in each height layer.

At 220, to determine or identify the pollution areas in a layer, a determination is made as to whether a distance between two pollution grids is less than a threshold distance.

In one embodiment, the identifying of a pollution area in a height layer is to determined whether $$Dist(\Delta lat, \Delta lon) < x$$

wherein Dist( ) is a distance between any two coordinate locations, i.e., a Δlat, Δlon, in which particulate matter has been found in a height layer, and "x" is a threshold distance within which the two grids are regarded in the same "pollution area."

Then, continuing at 225, for all pollutions areas at that layer, a determination is made as to whether the number of pollution areas is greater than a threshold number of area, i.e., whether:

$$a\ number\ of\ pollution\ areas > thresh$$

If, at 225, it is determined that the number of identified pollution areas at that height is not greater than a threshold number of areas, then, at 240, a determination is made as to whether there are any more height layers to process. If there are no more height layers to process, then the process ends. Otherwise, at 240, if it is determined that there are further height layers to process, then the next current height layer, e.g., a height layer h+1, is obtained at 245, and processing re-commences by returning back to step 205, to repeat running the processing steps 210-240 again at a next current height layer.

Otherwise, at 225, if it is determined that the number of identified pollution areas at that height is greater than a threshold number of areas, i.e., number of pollution areas > thresh, then, at 230, the respective areas can be recorded as Area1_h, Area2_h, . . . , etc., where h is the current height layer. Then, then, at 240, a determination is made as to whether there are any more height layers to process. If there are no more height layers to process, then the method ends. Otherwise, at 240, if it is determined that there are further height layers to process, then the next current height layer, e.g., a height layer h+1, is obtained at 245, and processing re-commences by returning back to step 205, to repeat running the processing steps 210-225 again at a next current height layer, e.g., height layer h+1.

Figure 3:
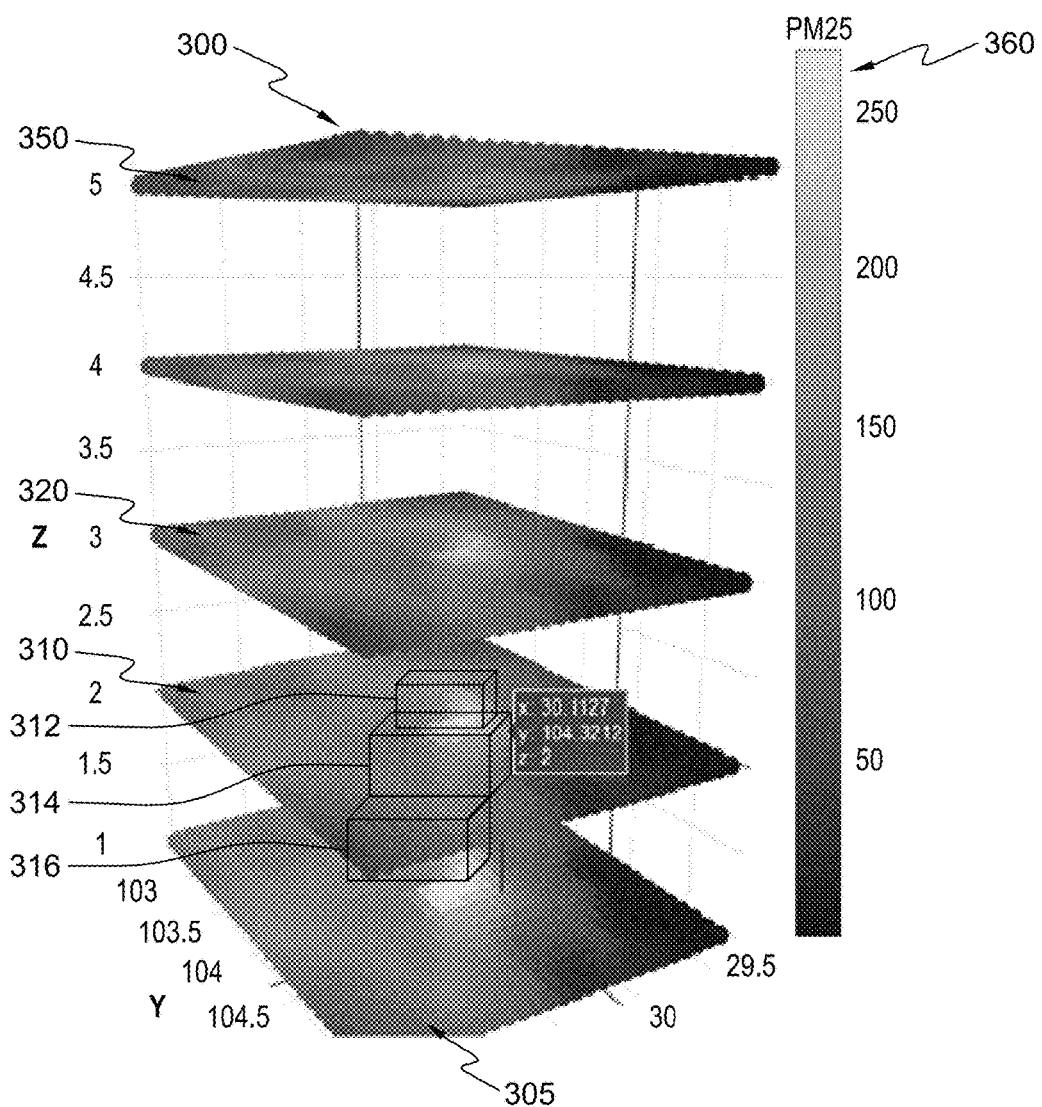
FIG. 3 depicts a defined air mass volume showing the results of processing method according to FIG. 2 for each height layers of a polluted air mass contour.

FIG. 3 shows a defined air mass 300 showing the results of processing method according to FIG. 2 for each of example height layers 305, 310, 320, etc. As shown, a height limit 350 is identified that represents a planetary boundary layer (PBL) height constraint.

FIG. 3 further shows the determined pollution (cubic) grids 312, 314, 316 where above-threshold concentrations of particulate matter, e.g., PM2.5, have been found, e.g., above and below example height layer 310 as shown. An accompanying legend 360 shows an embodiment of a color mapping scheme for mapping a color on the legend corresponding to a particulate matter concentration in a height layer of the air mass grid such that the number of pollution areas is determined at different locations (areas) within a height layer. In one embodiment, methods are implemented herein that identify time-series masses in a same cluster (e.g., color) to generate 3-D air pollution transmission path. For example, these pollution grids 312, 314 and 316 are 3-dimensional grids obtained from observed areas of pollution, e.g., areas Area1_h and Area2_h, by the ground-based and/or UAV-based pollution monitoring sensors. A 3-D contour of air pollution within the 3-D grid defining volume 300 is identified based on all the observed areas at different locations within all height layers. From the identified pollution (cubic) grids 312, 314, 316 having above-threshold concentrations of particulate matter, there may be identified a 3D-contour of pollution.

Figures 4, 5:
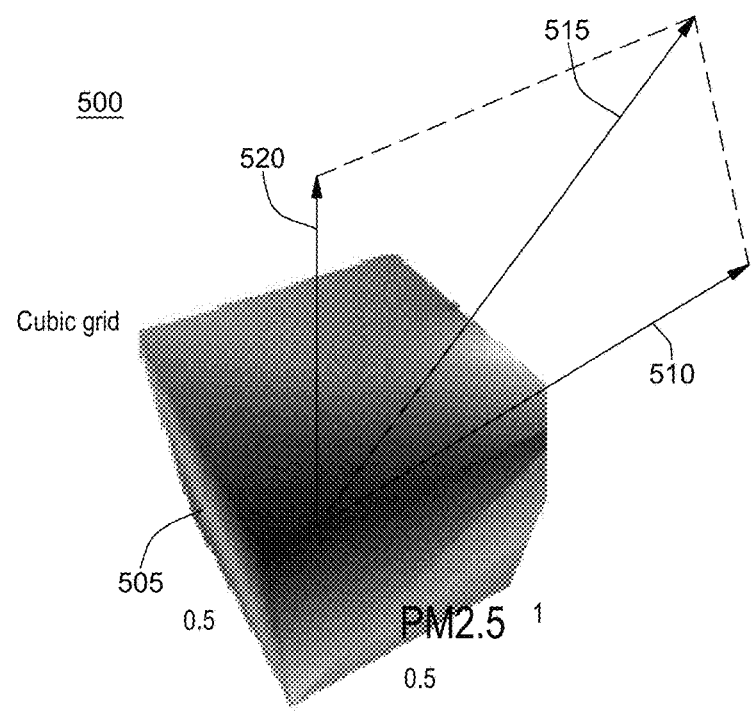
FIG. 4 depicts a chart showing example pollution areas (locations) at the various height levels, h1, h2, . . . , hn within a polluted air mass.
FIG. 5 shows an example decomposition of a cubic grid with mass concentration from the polluted air mass in which its displacement can be estimated in one embodiment.

FIG. 4 depicts a chart 400 showing recorded examples of pollution areas (locations) at the various height levels, h1, h2, . . . , hn within the air mass 300. For example, at a first height h1 405, there is depicted an area Area1_h1 410 having particulate matter found therein in amounts that exceed the set threshold and thus contribute to the air mass centroid. Additional areas at height level h1, i.e., Area2_h1, AreaM_h1 do not have particulate matter found therein in amounts that exceed the set threshold. Chart 400 may be completed after repeating method 200 of FIG. 2 to show, at each height level h2, . . . , hn, and corresponding areas therein having particulate matter (e.g., PM2.5) concentrations exceeding threshold amounts. For example, at height h2, a first area, Area1_h2, does not have particulate matter concentration exceeding threshold amount but a second area Area2_h2 415, does have particulate matter concentration exceeding threshold amount. Similarly, at the height hn, a first area Area1_hn 420 does have particulate matter concentration exceeding threshold amount. There overlapping areas of the identified pollution (cubic) grids having above-threshold concentrations of particulate matter are used to identify a 3D-contour of pollution.

In one embodiment, the processing performed at each height layer of FIGS. 2, 3 is performed at a first time instance, e.g., T1. In one embodiment, further processing includes invoking methods to determine the observed 3-D polluted air mass at a time T1, i.e., a Mass1_T1, by integrating the overlapped pollution area(s) in adjacent layers of height. In view of the chart found in FIG. 4, there is determined a mass centroid of the air mass at time T1, i.e., a value referred to as Mass1_T1, as the integration of the areas Area1, . . . , AreaM in heights h, . . . , hn having particulate matter concentrations determined to exceed the threshold concentration amount as shown in FIG. 3. In the example of FIG. 4, PM concentrations in areas 410, 415, 420 etc. will be integrated over the entire air mass 300 and a centroid of the polluted air mass determined at time instance T1, i.e., Mass1_T1.

Returning back to FIG. 1, step 115 performs the identifying of a location of a centroid of the air mass at the current time instant, e.g., T1. More particularly, the centroid location, $r_o$, of a 3-D polluted air mass 300 may be calculated by the quality m of each cubic grid (=PM2.5 concentration in a grid*grid volume) defining the contour according to equation 1) as follows:

$$r_\sigma = \frac{\sum_i m_i r_i}{M}, \qquad 1)$$

where, M is the total mass of the polluted air mass, and for each cubic grid i, the concentration (μg/m³) and the unit mass $m_i$ are obtained (i.e., according to concentration*grid volume). By selecting one fixed point, the distance $r_i$ between a pollution grid i with the fixed point is calculated, and then the centroid location, $r_o$ is obtained.

Returning back to FIG. 1, step 120 performs the estimating of a transport path or transmission path of the polluted air mass by integration of cubic grid displacement with Lagrangian method and Bernoulli equation (wind-pressure relationship) in a 3-D meteorologic condition.

As "wind" speed is one factor to make the air mass with suspended particles diffuse, it is assumed that the displacement of the particles is determined by a wind field. Then the location of the particle's trajectory can be obtained by implementing time-and-space integral calculus. In one embodiment, in a simplified form of the Lagrangian diffusion method, the location of the particle's trajectory is computed from an average of three-dimensional velocity vectors at an initial-position P(t) and a first-guess position P'(t+Δt) according to:

$$P'(t+\Delta t)=P(t)+V(P,t)\Delta t$$

where V is a velocity vector (wind speed). In one embodiment, the velocity vectors are linearly interpolated in both space and time. The integration time step (Δt) can vary during simulations performed at the computing system of FIG. 10. In one embodiment the time step is computed from the requirement that an advection distance per time-step should be less than a grid spacing.

The displacement of each cubic grid in T1-observed polluted air mass to a T2 time is estimated with computer processes applying a Lagrangian method and the Bernoulli equation that describes a wind-pressure relationship. In one embodiment, the wind speed to the cubic grid in 3-D space is calculated by synthesis of a horizontal and vertical wind vector, such as may be obtained from NCEP FNL (Final) Operational Global Analysis data (managed by the Data Support Section of the Computational and Information Systems Laboratory at the National Center for Atmospheric Research in Boulder, Colo.) or like numerical weather prediction model (e.g. Weather Research and Forecasting (WRF) Model).

FIG. 5 depicts an example decomposition 500 of an example PM2.5 polluted cubic grid 505 with mass concentration from the polluted air mass in which its displacement can be estimated with its initial velocity and the accelerated velocity by dynamic pressure from 3-D wind. That is, using cubic grid decomposition, a displacement estimation of cubic grid 505 along horizontal and vertical directions can be found according to the obtained wind field from a numerical model, e.g., represented by a combined wind vector V 515 (e.g., in m/s) having horizontal wind force component vector 510 and vertical wind force component 520, and the mass concentration of the grid.

According to wind-pressure relationship set forth in the Bernoulli equation, the dynamic pressure from 3-D wind is governed according to equation 2) as follows:

$$wp=0.5 \cdot \rho \cdot V^2 \qquad 2)$$

where wp is wind-pressure (e.g., in $kN/m^2$), $\rho$ is the air (mass) density (e.g., in $kg/m^3$), and V is the wind speed (e.g., in m/s). The air density is obtained from available meteorological temperature and pressure data for that location/time according to the following equation:

air density=1.293*(Pressure/1atm)*(273.15/absolute temperature)

where absolute temperature=degree Celsius+273.15. FIG. 9 shows an example air density table 900 showing example air temperature and pressure conditions and corresponding air density computations as available from on-line sources. Continuing with the processing at step 120, there is computed the Δt-displacement according to equation 3) as follows:

$$\Delta S = v0 \, \Delta t + \tfrac{1}{2} a \Delta t^2 \qquad 3)$$

where the accelerated velocity a=wp*S/(C*Vgrid), C is the PM2.5 concentration in this grid, S is the stressed area, and Vgrid is the cubic grid's volume.

Then, a transport of the air pollution from T1 to T2 time is estimated by integration of cubic grid displacement. In one embodiment, the T2-estimated air mass, e.g., Mass2_T1, and particularly the T2-estimated grids are kept in continuous air mass. Any dispersed T2-estimated grids are removed from the air mass. Additionally removed are the T2-estimated grids estimated to be transported above the PBL height when the corresponding T1-observed grids are under the PBL height. In one embodiment, these T1-observed grids below the PBL height can not reach the PBL height due to the constraint of vertical diffusion of particles within local PBL height.

Figure 6:
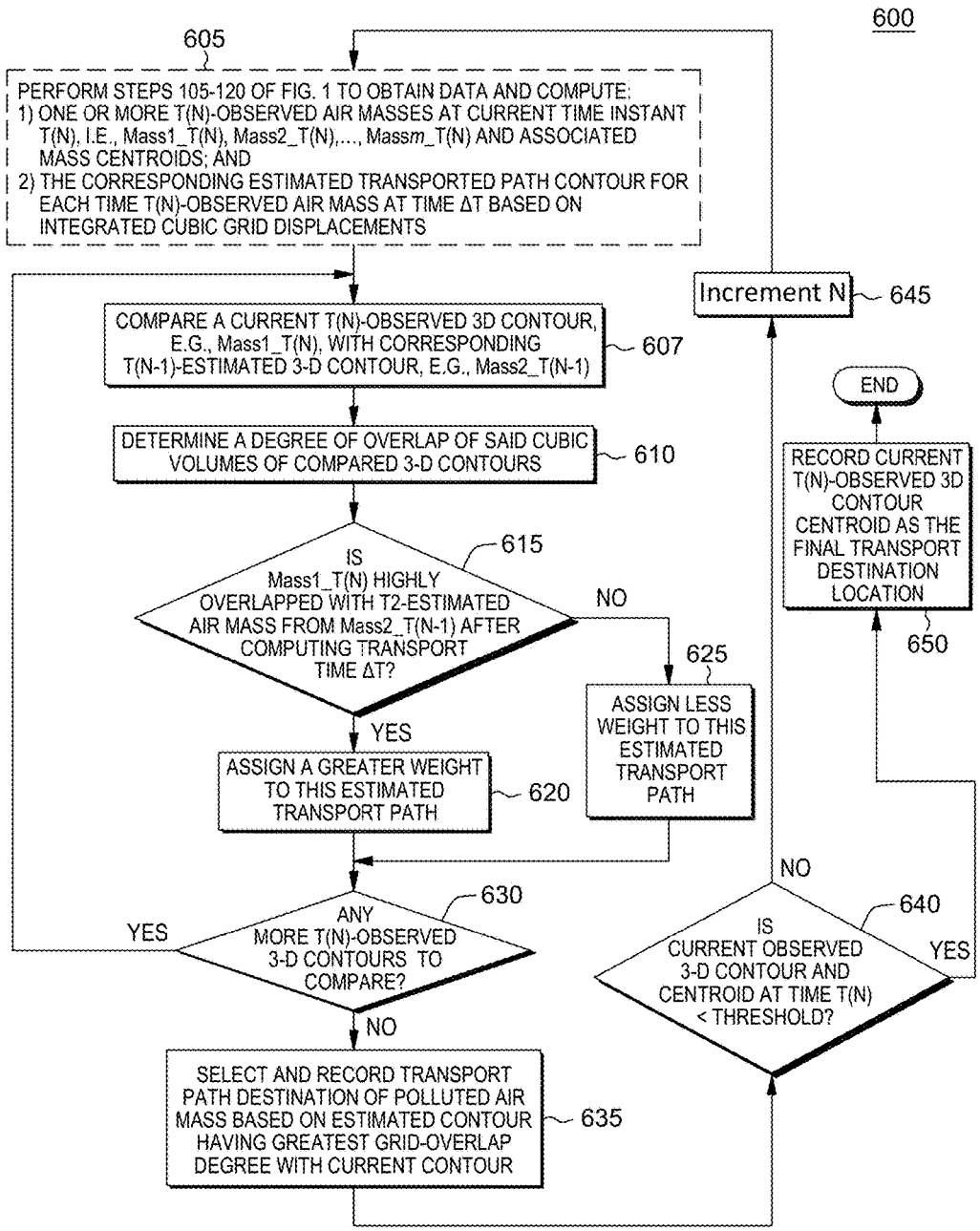
FIG. 6 show a method for determining the main air pollution transmission path using both estimated and observed destinations in one embodiment.

FIG. 6 show a method for determining the main air pollution transmission path using both estimated and observed destinations such as described at step 125, FIG. 1. FIG. 6 depicts an iterative method, in which the main (polluted air mass) transporting locations in times T1~Tn can be determined successively.

First, at 605, FIG. 6, there is performed the observing and identifying one or more current 3-D contour(s) of pollution at a current location and extracting a mass centroid from each, e.g., Mass1_T(N), Mass2_T(N), . . . , Massm_T(N), based on 3-D cubic grid data of PM2.5 observed concentration in a current (next) time instance after transport time interval Δt. Steps 105-120 of FIG. 1 may be used to perform this. Additionally obtained are the prior corresponding estimated contour path destinations for each current 3-D contour computed for the transport time interval Δt (T(N)-T(N-1)) based on respective prior time T(N-1)-observed 3-D contour(s) (e.g., Mass1_T(N-1), Mass2_T(N-1), . . . , Massm_T(N-1)). Then, at 607, a comparison is made of a current T(N)-observed 3D contour, e.g., Mass1_T(N), with a time T(N-1)-estimated 3-D contour, e.g., Mass2_T(N-1), and, at 610, a determination is made as to a degree of grid overlap between the current observed Mass1_T(N) with one of the prior estimation transported air mass 3-D contours, e.g., Mass2_T(N-1), which degree of overlap is used to determine a strength of the transport path between successive time instants.

Figures 7, 8:
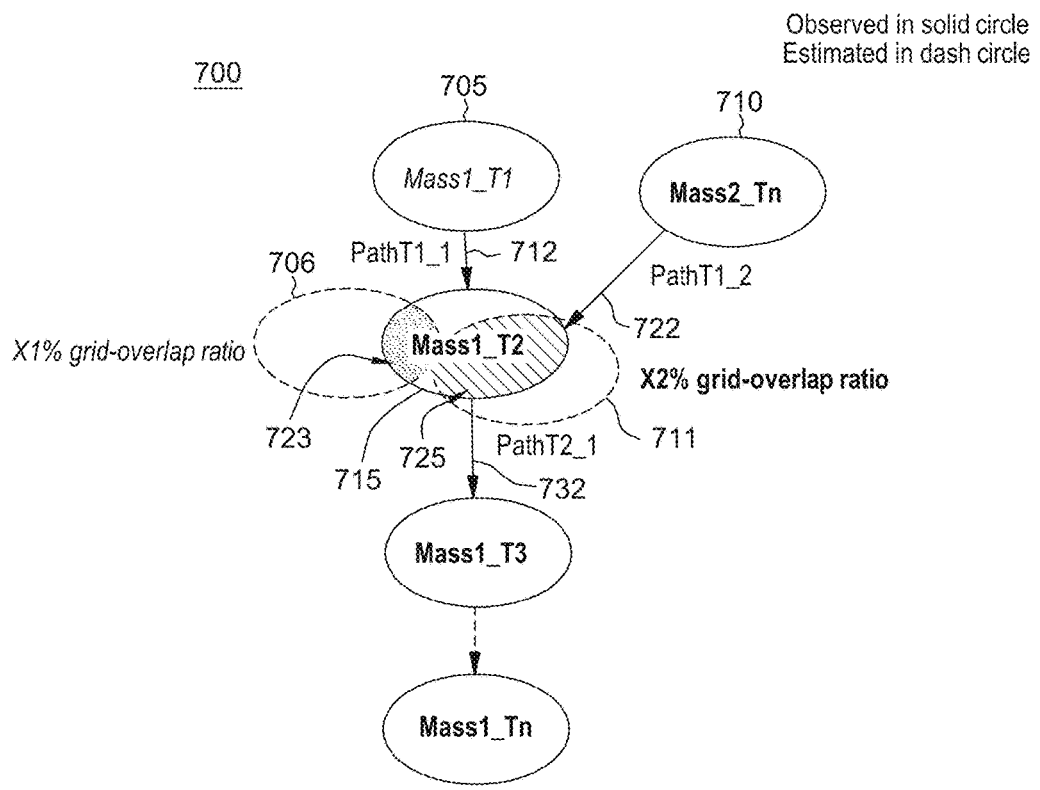
FIG. 7 conceptually shows a determining of a degree of overlap between an observed with the estimated in determining a main transport path of the polluted air mass between successive time instances.
FIG. 8 shows in one embodiment a table data structure storing the computed mass centroids obtained from the processes shown in FIG. 6.

Then continuing to step 615, FIG. 6, a determination is made as to whether Mass1_T(N) is highly overlapped with T2-estimated air mass from Mass2_T(N-1) after computing transport time Δt. For example, at 605, there may be obtained a time T2-observed current 3-D contour (of actual displaced or transported polluted cubic volumes) and obtained corresponding mass centroid at T2, i.e., Mass1_T2. At 610, this may be compared to the T2-estimated 3-D contour based on a determined transport time Δt (and based on recorded wind and meteorological condition data), and having a computed mass centroid, e.g., Mass2_T1. As shown in FIG. 7, the degree of overlap is computed to ascertain a strength of these potential transport paths for the air mass between the time instants T1-T2 (=Δt).

In one embodiment, the Δt=T2-T1 may be set as 10.0 minutes, or any other time interval. For example, the Δt may be the conventional time interval of meteorologic and pollution data, e.g., 1 hour. In one embodiment, data can be interpolated to a shorter time step of 10 min. for higher resolution calculations.

FIG. 7 conceptually shows the determination of a degree of overlap 700 between the current observed polluted air mass Mass1_T2 715 at time T2 (=time T(N)) with one of the estimated contours from the prior time instant, e.g., Mass1_T1 705, Mass2_T1 710, etc. at time T1 (=time T(N-1)), in determining a main transport path for the polluted air mass. For example, based on the degree of overlap, either a transport path, e.g., PathT1_1 712 corresponding to a transport of the polluted air mass T1-observed Mass1_T1 705 or a path PathT1_2 722 corresponding to a transport of the polluted air mass T1-observed Mass2_T1 710 is selected as the transport path for the air mass between time instances T1-T2.

Whether the time T2-observed air mass value, i.e., Mass1_T2 715, is highly overlapped with a T2-estimated air mass, e.g., Mass1_T1 705, Mass2_T1 710, etc. after the computed transport time Δt=T2-T1 is determined using the processes leading up to and including equations 1)-3) for estimating air mass transport by integration of cubic grid displacement. As shown in FIG. 7, as an example, the current T2-observed air mass value Mass1_T2 715 is determined more highly overlapped with T2-estimated air mass 711 from Mass2_T1 710 after Δt=T2-T1 transport (transport estimation), as would be indicated by a higher computed grid-overlap ratio (X2%) 725. In comparison, the grid-overlap with T2-estimated air mass 706 from Mass1_T1 705 after transport time Δt indicates a lower computed grid-overlap ratio (X1%) 723.

Thus, returning to 615, FIG. 6, based on the results of the comparison between estimated and observed 3-D polluted air mass contours, an associated weight will be assigned to the respective path based on the determined degree of overlap.

In the example of FIG. 7, with the higher grid-overlap ratio determined with these estimated and observed 3-D contours, it is regarded that T2-observed air mass Mass1_T2 715 is partly generated by the transport of T1-observed air mass, i.e., Mass2_T1 710, and the method at 620, FIG. 6 assigns a larger transport weight to this transport path 722 between time instant T1 and T2. That is, the greater degree of overlap, then the less difference there is between the averaged original PM2.5 value and destination value, and the more weight for this associated path.

Otherwise, if at 615, FIG. 6 the new T2-observed air mass Mass1_T2 715 is overlapped less with T2-estimated air mass 706 from Mass1_T1 705 after Δt=T2−T1 transport (transport estimation), as shown in FIG. 7, it is regarded that T2-observed air mass Mass1_T2 715 is not partly generated by the transport of T1-observed air mass, i.e., Mass1_T1 705, and the method at 625, FIG. 6 assigns a smaller transport weight to this transport path 712 between time instant T1 and T2. That is, the less degree of overlap, then the greater the difference there is between the averaged original PM2.5 value and destination value, and the less weight assigned for this path.

In one embodiment, a transport weight for a path, e.g., a PathT1_X (at time T1 or any time instant such as shown in FIG. 7) may be computed according to the following expression:

Transport weight of PathT1_$X$=$w1$*grid-overlap ratio+$w2$/abs(avg(PM2.5inOverlapPart)−avg (PM2.5inMassX_$T1$))

where X=1, 2, . . . , m, for time T1, and w1 and w2 (>0) are coefficients for the two factors.

Continuing to step 630, FIG. 6, a determination is made as to whether there are any more transport paths to compare current time T(N)-observed 3-D contours to compare grid-overlap between corresponding time T(N−1)-estimated 3-D contours for the transport time Δt. For example, it may be the case that several time T1-observed masses transport and then merge into one time T2-observed air mass. In this embodiment, the method of FIG. 6 generates a transport weight for each air mass based on respective computed grid-overlap ratios, and based on the ratios, selects a main transport path.

Thus, at 630, if there are more transport paths to compare, then the method returns to step 607, FIG. 6, and repeats all steps 607-630 until no more current time T(N)-observed 3-D contours remain to compare. At such time, the method proceeds to step 635 to select transport path destination of the polluted air mass based on estimated contour having greatest grid-overlap degree with the current contour and record the current observed 3-D contour centroid and path.

Continuing to 640, FIG. 6, a determination is made as to whether the current observed 3-D contour and computed centroid at time T(N)<threshold particulate matter concentration level. If the current observed 3-D contour and computed centroid at time T(N) still has PM2.5 concentrations exceeding acceptable threshold level, then the process repeats to determine the next destination of the transport path of air mass 300. At 645, the time instant N is incremented (i.e., N=N+1) and the process is repeated for a next transport time interval Δt by returning to step 605. Then, all steps of FIG. 6 are repeated to determine the next transport path (transport destination) based on the next T(N+1)-observed 3D contour, e.g., Mass1_T(N+1). For the example, this next observed 3D contour will be determined at the Δt=T3−T2 transport interval having a centroid Mass1_T3 and associated estimated transport path PathT2_1 732. The iterative process steps 605-645 is continued until a final transport path 742 is determined for an observed 3-D pollution contour having a centroid mass Mass1_Tn.

In one embodiment, the iterative process steps 605-645 is continued until at 640, it is determined that the current observed concentration in the transported polluted air mass is less than an acceptable threshold PM2.5 concentration level, e.g., corresponding to acceptable quality air. At such time, the process will proceed to step 650 to record the location of the current T(N)-observed 3D contour as the final transport destination location of the original polluted air mass and the process ends.

As a result of the processing of FIG. 6, the system has generated and recorded in a memory device, the computed mass centroid values computed for each one or more 3-D contours observed at each time instant, T=T1, T2, . . . , Tn (e.g., N=1, 2, . . . , n) and their corresponding coordinate locations, e.g., a latitude and longitude. That is, for all time instants T(N), there is recorded all computed mass centroids and their locations for all observed 3-D contours.

FIG. 8 shows in one embodiment, a table data structure 800 storing the computed centroids, e.g., Mass1_T1, Mass2_T1, . . . , Massm_T1 for time T1; Mass1_T2, Mass2_T2, etc. for time T2, etc. until the last iteration which records Mass1_Tn, Mass2_Tn, etc. for time Tn. The sequence depicted by successively selected contours having determined mass centroids Mass2_T1 805, Mass1_T2, 810 and Mass1_Tn 829 represent the transport path destinations of the polluted air mass at each successive time interval Δt.

Thus, by the iterative process of FIG. 6, the main transporting locations at successive times T1~Tn can be determined by the successive observed 3-D contours having greatest degree of grid-overlap. The main 3-D air pollution transmission path can be obtained by connecting the 3-D air mass's centroids during its time-series destination locations as shown by connected centroids in FIG. 8. In one embodiment, the determination of the "Main" transport path is obtained by integrating each step path with maximum transport weight, as follows:

Main Path=Max(Transport weight of PathT1_$X$)-> Max(Transport weight of PathT2_$X$-> . . . -> Max(Transport weight of Path $Tn\_X$)

In one embodiment, the system, methods and iterative processes described herein may be used to provide dynamic control of polluting sources. For example, by continually recording various meteorological and wind condition data over time, a computational model may be generated that relates various historical wind field, meteorological conditions and PLB height constraint data affecting displacement of masses of polluted air, and particularly, their transport or transmission path(s). Then, given historical wind/meteorological conditions correlated with main transmission paths of polluted air masses, a transport of a current polluted air mass at an initial location may be predicted. From this prediction, a source(s) of pollution that provide the concentration levels of particulates observed in the air mass at the initial location can be dynamically controlled.

That is, a given input of real-time current or expected wind field condition data, meteorological condition data and PLB constraint condition at an initial location may be compared with past historical scenarios of like wind and meteorological conditions for which a respective historical transmission path(s) of polluted air mass(es) between initial and final locations has(have) been already determined. That is, using the computational model, based on the comparing of the current input real-time wind condition data against the historic wind condition data and given any current particulate matter concentrations levels, signals may be automatically generated to trigger a pollution source to increase or decrease a frequency of particulate emission or particulate generating, or control an amount of particulates generated at the respective pollution source(s) in order to preserve or maintain a particulate concentration level at a various location(s) to within a specified level. These steps may be performed to regulate air quality at anywhere along a transport path corresponding to a similar historic transmission path for the similar historical wind field and meteorological conditions.

Figure 10:
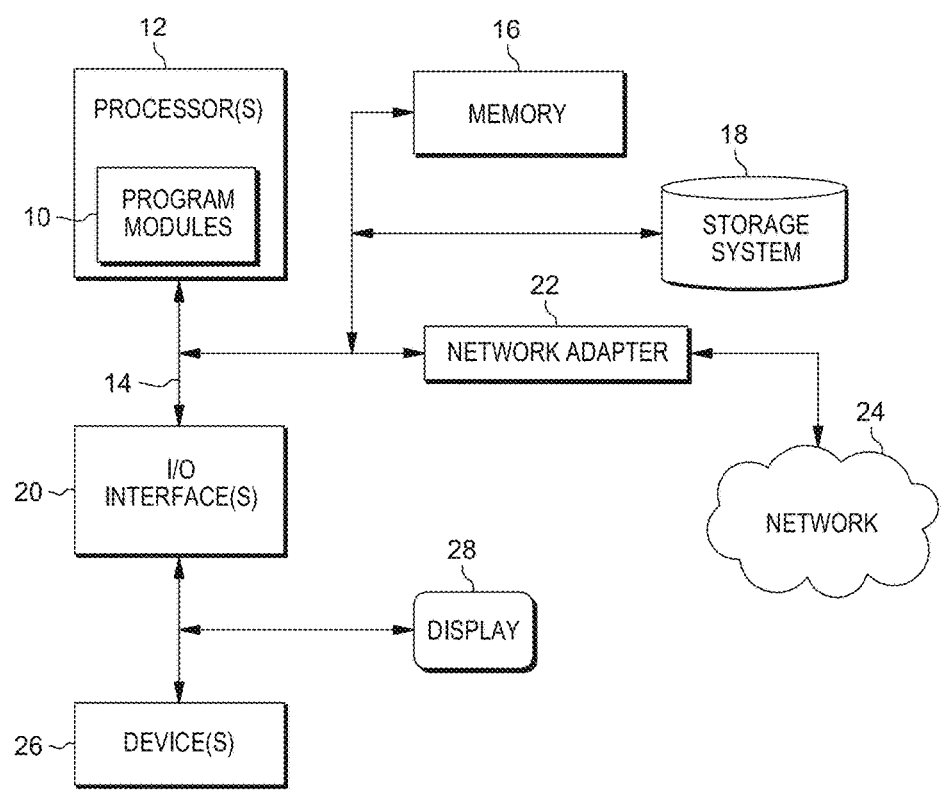
FIG. 10 illustrates an exemplary computing apparatus for determining a main transport path of the polluted air mass in accordance with the embodiments of the present invention.

FIG. 10 illustrates an example computing system in accordance with the present invention. It is to be understood that the computer system depicted is only one example of a suitable processing system and is not intended to suggest any limitation as to the scope of use or functionality of embodiments of the present invention. For example, the system shown may be operational with numerous other general-purpose or special-purpose computing system environments or configurations. Examples of well-known computing systems, environments, and/or configurations that may be suitable for use with the system shown in FIG. 10 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

In some embodiments, the computer system may be described in the general context of computer system executable instructions, embodied as program modules stored in memory 16, being executed by the computer system. Generally, program modules may include routines, programs, objects, components, logic, data structures, and so on that perform particular tasks and/or implement particular input data and/or data types in accordance with the present invention (see e.g., FIG. 2).

The components of the computer system may include, but are not limited to, one or more processors or processing units 12, a memory 16, and a bus 14 that operably couples various system components, including memory 16 to processor 12. In some embodiments, the processor 12 may execute one or more modules 10 that are loaded from memory 16, where the program module(s) embody software (program instructions) that cause the processor to perform one or more method embodiments of the present invention. In some embodiments, module 10 may be programmed into the integrated circuits of the processor 12, loaded from memory 16, storage device 18, network 24 and/or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer system may include a variety of computer system readable media. Such media may be any available media that is accessible by computer system, and it may include both volatile and non-volatile media, removable and non-removable media.

Memory 16 (sometimes referred to as system memory) can include computer readable media in the form of volatile memory, such as random access memory (RAM), cache memory an/or other forms. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

The computer system may also communicate with one or more external devices 26 such as a keyboard, a pointing device, a display 28, etc.; one or more devices that enable a user to interact with the computer system; and/or any devices (e.g., network card, modem, etc.) that enable the computer system to communicate with one or more other computing devices. Such communication can occur via Input/Output (I/O) interfaces 20.

Still yet, the computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with the computer system. Examples include, but are not limited to: microcode, device drivers, redundant processing units, external disk drive arrays, RAID systems, tape drives, and data archival storage systems, etc.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A system for determining a main transmission path of a polluted air mass comprising:
   one or more sensors for measuring a concentration level of particulates in an air mass at one or more locations; and
   at least one processor and a memory coupled to the at least one processor, wherein the memory comprises instructions which, when executed by the at least one processor, cause the at least one processor to:
   determine a current 3-D contour of pollution at the initial location and an initial time instant, said current 3-D contour having one or more cubic volumes of polluted air based on the measured particulate concentration levels of the air mass at said initial location;

compute, based on a received wind field condition data, an estimated 3-D contour of pollution for a next time instant and at a next destination location, said next destination determined based on estimated transport destinations of one or more cubic volumes of polluted air of said current 3-D contour from the initial location due to a wind field condition;

determine a next current 3-D contour of pollution at the next destination location and at said next time instant, said next current 3-D contour having one or more cubic volumes of polluted air based on new measured particulate concentration levels of an air mass at said next destination location; and determine a transport path of said polluted air mass from the initial location to the next destination location at said next time instant, wherein, to determine a transport path, said at least one processor computes a degree of transport weight overlap between cubic volumes of polluted air corresponding to the estimated 3-D contour of pollution at said next destination location and cubic volumes of polluted air corresponding to said determined current 3-D contour at said next time instant; and iterate, at each of next successive time instances and locations, the computing of an estimated 3-D contour of pollution to determine a transport path of said polluted air mass, subject to said wind field condition, at each successive next location, connect each transport path of said polluted air mass determined at each iteration to determine a main transmission path of said polluted air mass from said initial location to a final location; and dynamically control a source of pollution configured to provide said concentration levels of particulates observed in said air mass at said initial location, wherein to dynamically control, said at least one processor is further configured to:

obtain a past main transmission path of a polluted air mass between initial and final locations based on historic wind and meteorological condition data;

compare a current input real-time wind condition data against said similar historic wind condition data; and control an increase or decrease an amount of particulates generated at said pollution source based on said comparing.

2. The computer-implemented system of claim 1, wherein to iterate the computing of an estimated 3-D contour of pollution to determine a transport path, said at least one processor device is further configured to:

iterate, at each time instant of successive time instances:

the computing of an estimated 3-D contour of pollution for a next time instant and at a next destination location, wherein an initial location of a current iteration corresponds to a next destination location of an immediate prior iteration;

the determining of a next current 3-D contour of pollution at the next destination location based on measured particulates in said air mass at said next destination location; and the determining of a transport path of said polluted air mass between the initial location to the next current destination location for the current iteration.

3. The computer-implemented system according to claim 1, wherein said at least one processor is further configured to:

continually record various meteorological and wind condition data over time in the memory;

generate a model to correlate various recorded historical wind field and meteorological conditions data that resulted in displacement of masses of polluted air along connected transport paths forming a main transmission path between said initial and final locations; and run said model to estimate a transport of a polluted air mass currently at an initial location.

4. The computer-implemented system of claim 2, wherein during said iterating, said at least one processor is further configured to:

determine whether concentration levels of particulates at an air mass at said next current destination location drops below a pre-set threshold concentration of particulates; and determine a final transport destination as said next destination location when said concentration levels at said next destination location are determined below the pre-set threshold concentration of particulates.

5. The computer-implemented system according to claim 3, wherein responsive to comparing a current input real-time wind condition data against said similar historic wind condition data, said at least one processor is further configured to:

automatically generate a trigger signal to trigger a pollution source to control an amount of particulates generated at the respective pollution source(s) such that a particulate concentration level is maintained at a location along the transport path is to within a specified level.

6. The computer-implemented system according to claim 4, wherein said at least one processor is further configured to:

receive input data comprising locally observed concentration levels of particulates at different layers of an air mass and at different locations within each said layer at a time instant;

based on said input data, identify a 3-D contour of pollution in said air mass at an initial location, said contour having one or more cubic volumes of pollution based on observed concentration levels of particulates exceeding a threshold level at said time instant;

identify, based on said received input data, additional 3-D contours of pollution at respective additional initial locations, each said additional 3-D contour having one or more cubic volumes of pollution based on observed concentration levels of particulates exceeding a threshold level at said time instant at each said additional initial locations; and for each additional 3-D contour of pollution, based on said received wind field condition data, compute an estimated transport destination of said one or more cubic volumes of polluted air at said next time instant in each respective said additional 3-D contour; and for each additional 3-D contour of pollution:

compute a corresponding estimated 3-D contour of pollution at said subsequent time instant, each respective said corresponding estimated 3-D contour based on estimated transport destinations of said one or more cubic volumes of polluted air within each; and determining a degree of transport weight overlap between cubic volumes of polluted air corresponding to the estimated 3-D contour of pollution and cubic volumes of polluted air corresponding to the current 3-D contour of pollution at said current destination location and said next time instant; and select the transport path of a polluted air mass from one of said additional initial locations to the current destination location based having a greatest degree of transport weight overlap.

7. The computer-implemented system according to claim 6, wherein said at least one processor is further configured to:
   determine a merge of two or more said additional 3-D contours of pollution that form said current 3-D contour of pollution at said current destination location at said subsequent time instant; and
   select a main transport path of a polluted air mass from one of said additional initial locations based on a respective degree of transport weight overlap of each respective transport path with said current 3-D contour of pollution.

8. A computer program product for determining a main transmission path of a polluted air, the computer program product comprising a computer-readable storage medium having a computer-readable program stored therein, wherein the computer-readable program, when executed on a processor, causes the processor to:
   determine a current 3-D contour of pollution at an initial location and an initial time instant, said current 3-D contour having one or more cubic volumes of polluted air based on measured particulate concentration levels of an air mass at said initial location;
   compute, based on received wind field condition data, an estimated 3-D contour of pollution for a next time instant and at a next destination location, said next destination determined based on estimated transport destinations of one or more cubic volumes of polluted air of said current 3-D contour from the initial location due to a wind field condition; determine a next current 3-D contour of pollution at the next destination location and at said next time instant, said next current 3-D contour having one or more cubic volumes of polluted air based on new measured particulate concentration levels of an air mass at said next destination location; and
   determine a transport path of said polluted air mass from the initial location to the next destination location at said next time instant, wherein, to determine a transport path, said at least one processor computes a degree of transport weight overlap between cubic volumes of polluted air corresponding to the estimated 3-D contour of pollution at said next destination location and cubic volumes of polluted air corresponding to said determined current 3-D contour at said next time instant; and
   iterate, at each of next successive time instances and locations, the computing of an estimated 3-D contour of pollution to determine a transport path of said polluted air mass, subject to said wind field condition, at each successive next location,
   connect each transport path of said polluted air mass determined at each iteration to determine a main transmission path of said polluted air mass from said initial location to a final location; and
   dynamically control a source of pollution configured to provide said concentration levels of particulates observed in said air mass at said initial location, wherein to dynamically control, said at least one processor is further configured to:
   obtain a past main transmission path of a polluted air mass between initial and final locations based on historic wind and meteorological condition data;
   compare a current input real-time wind condition data against said similar historic wind condition data; and
   control an increase or decrease an amount of particulates generated at said pollution source based on said comparing.

9. The computer program product of claim 8, wherein to iterate the computing of an estimated 3-D contour of pollution to determine a transport path, the computer-readable program, when executed on a processor, further causes the processor to:
   iterate, at each time instant of successive time instances:
      the computing of an estimated 3-D contour of pollution for a next time instant and at a next destination location, wherein an initial location of a current iteration corresponds to a next destination location of an immediate prior iteration;
      the determining of a next current 3-D contour of pollution at the next destination location based on measured particulates in said air mass at said next destination location; and
      the determining of a transport path of said polluted air mass between the initial location to the next current destination location for the current iteration.

10. The computer program product of claim 8, wherein said computer-readable program, when executed on a processor, further causes the processor to:
   determine a merge of two or more said additional 3-D contours of pollution that form said current 3-D contour of pollution at said current destination location at said subsequent time instant; and
   select a main transport path of a polluted air mass from one of said additional initial locations based on a respective degree of transport weight overlap of each respective transport path with said current 3-D contour of pollution.

11. The computer program product of claim 8, wherein said computer-readable program, when executed on a processor, further causes the processor to:
   continually record various meteorological and wind condition data over time in the memory;
   generate a model to correlate various recorded historical wind field and meteorological conditions data that resulted in displacement of masses of polluted air along connected transport paths forming a main transmission path between said initial and final locations; and
   run said model to estimate a transport of a polluted air mass currently at an initial location.

12. The computer program product of claim 9, wherein said computer-readable program, when executed on a processor, further causes the processor to:
   during said iterating:
   determine whether concentration levels of particulates at an air mass at said next current destination location drops below a pre-set threshold concentration of particulates; and
   determine a final transport destination as said next destination location when said concentration levels at said next destination location are determined below the pre-set threshold concentration of particulates.

13. The computer program product of claim 11, wherein to responsive to comparing a current input real-time wind condition data against said similar historic wind condition data, said said computer-readable program, when executed on a processor, further causes the processor to:
   automatically generate a trigger signal to trigger a pollution source to control an amount of particulates generated at the respective pollution source(s) such that a particulate concentration level is maintained at a location along the transport path is to within a specified level.

14. The computer program product of claim 12, wherein said computer-readable program, when executed on a processor, further causes the processor to:

receive input data comprising locally observed concentration levels of particulates at different layers of an air mass and at different locations within each said layer at a time instant;

based on said input data, identify a 3-D contour of pollution in said air mass at an initial location, said contour having one or more cubic volumes of pollution based on observed concentration levels of particulates exceeding a threshold level at said time instant;

identify, based on said received input data, additional 3-D contours of pollution at respective additional initial locations, each said additional 3-D contour having one or more cubic volumes of pollution based on observed concentration levels of particulates exceeding a threshold level at said time instant at each said additional initial locations; and for each additional 3-D contour of pollution, based on said received wind field condition data, compute an estimated transport destination of said one or more cubic volumes of polluted air at said next time instant in each respective said additional 3-D contour; and for each additional 3-D contour of pollution:

compute a corresponding estimated 3-D contour of pollution at said subsequent time instant, each respective said corresponding estimated 3-D contour based on estimated transport destinations of said one or more cubic volumes of polluted air within each; and determining a degree of transport weight overlap between cubic volumes of polluted air corresponding to the estimated 3-D contour of pollution and cubic volumes of polluted air corresponding to the current 3-D contour of pollution at said current destination location and said next time instant; and select the transport path of a polluted air mass from one of said additional initial locations to the current destination location based having a greatest degree of transport weight overlap.

* * * * *